(12) United States Patent
Matsutani et al.

(10) Patent No.: US 6,702,578 B2
(45) Date of Patent: *Mar. 9, 2004

(54) DENTAL HANDPIECE

(75) Inventors: Kanji Matsutani, Takanezawa-machi (JP); Nozomu Satake, Takanezawa-machi (JP); Toshiyuki Takase, Takanezawa-machi (JP)

(73) Assignee: Mani, Inc., Tochigi (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/910,062

(22) Filed: Jul. 20, 2001

(65) Prior Publication Data

US 2002/0018979 A1 Feb. 14, 2002

(30) Foreign Application Priority Data

Jul. 24, 2000 (JP) ........................................ 2000-221941

(51) Int. Cl.[7] ................................................. A61C 3/00
(52) U.S. Cl. .......................... 433/75; 433/102; 433/224
(58) Field of Search ............................... 433/75 OR, 76, 433/102 R, 116, 224 R

(56) References Cited

U.S. PATENT DOCUMENTS

| | | | | |
|---|---|---|---|---|
| 1,321,129 A | * | 11/1919 | Schlueter | 433/76 |
| 2,621,408 A | * | 12/1952 | Klein | 433/76 |
| 4,571,183 A | * | 2/1986 | Nash | 433/116 |
| 4,778,387 A | * | 10/1988 | Komatsu | 433/116 |
| 4,940,410 A | * | 7/1990 | Apap et al. | 433/102 |
| 5,586,886 A | * | 12/1996 | Roane | 433/224 |

* cited by examiner

*Primary Examiner*—John J. Wilson
(74) *Attorney, Agent, or Firm*—Muramatsu & Associates

(57) ABSTRACT

A dental handpiece stably cutting a wall of a root canal without a fear of piercing a root opening. The dental handpiece includes a means for holding a tool cutting a tooth to be cured and a support for setting the cutting tool at a desired position relative to the tooth to be cured. The length of the support may be changeable by stages. The holding means may be formed of a head of the dental handpiece and a plurality of supports with different lengths may be removably mounted to the head. The support can stand on a head of the dental handpiece and the length from the head is changeable. The support is formed separately from the dental handpiece to be removable, and may have a stopper which abut with a tooth to be cured or an appropriate portion near the tooth.

5 Claims, 7 Drawing Sheets

DENTAL HANDPIECE

BACKGROUND OF THE INVENTION

1. Field of the Invention

The present invention relates to a handpiece for dental use, and more particularly, to a handpiece to be used by a dentist for cutting or drilling a root canal of a tooth.

2. Description of the Related Art

In forming a root canal of a tooth, a dental reamer or a dental file (hereinafter referred to as "cutting tool") is generally used. The cutting tool may be operated manually or with use of a handpiece with a drive mechanism. With these cutting tools, a spiral cutting edge is inserted into a root canal, and the back and forth movements or rotational movements of the cutting tools by changing the cutting tools corresponding to the shape of the root canal allows the root canal to be tapered. To cut a root canal, a handle of a cutting tool is held for manual operation, or a cutting tool is connected to a dental handpiece for using rotationally driving force of motor or the like.

Since a dental reamer has a large lead, that is, a relatively gentle spiral cutting edge, it is mainly used for cutting by rotational movements. In contrast, a dental file has a spiral cutting edge having a lead smaller than that of the dental reamer, therefore, it is mainly used for cutting through back and forth movements like a file. Further, the dental file is often used by incorporating the back and forth movements as well as some rotational movements at the same time, which allows a root canal to be cut by the back movement and debris generated by the cutting to be carried away to outside of the root canal through spiral channels of the edge portion.

A dental handpiece heretofore in use for operating these cutting tools is sometimes capable of driving the tools both by the back and forth movements and by the rotational movement. "The back and forth movements" means the movements of the cutting tools for cutting by the back and forth movements, that is, reciprocating movement in a longitudinal direction of the cutting tools. In a dental handpiece in the past, when an edge portion of a cutting tool is caught by a curved portion of a root canal or the like, the cutting tool does not progress further from the caught portion and stays there, therefore, only a head of the dental handpiece relatively goes up and down, which causes the root canal not to be cut at all.

Further, when the cutting tool is forced to be depressed, it is cut into a wall of the root canal and fixed thereto, therefore, the cutting tool does not move any more, which causes a vicious circle in which only the dental handpiece to be liable to go up and down. If the edge portion of the cutting tool is cut into the wall of the root canal, the edge portion may be damaged or broken. Still further, when only the dental handpiece goes up and down, a hand holding the handpiece vibrates, so that it becomes difficult to maintain the posture for cutting operation, which may cause an abuse such as the shift of the position to be processed.

Further, in case that the cutting tool reaches a portion near a root as the cutting operation proceeds, the cutting operation at the portion also mainly relies on the feeling of a dentist, so that the cutting tool may pierce the apical foramen of the dental root. If the cutting tool pierces the apical foramen of the dental root, osteomyelitis or periodontitis may occur, therefore, the phenomenon must be avoided.

In a dental handpiece rotating only one direction, that is, either normal or reverse direction, or reciprocally rotating both normal and reverse directions, that is, so called twist handpiece, a spiral cutting edge portion of the cutting tool proceeds while rotating by a driving source such as a motor, and the force of the driving source causes the edge portion of the cutting tool to be cut into a wall of a root canal and to rapidly be drawn toward a apical foramen of the dental root. As a result, there is a fear that the cutting tool pierces the apical foramen of the dental root or the cutting tool is damaged or broken since the edge portion is excessively cut into the wall of the root canal and locked thereto. Besides, the cutting tool forcibly proceeds, so that smooth root canal cannot be formed, and the surface of the wall is spirally scratched (tapping phenomenon), resulting in a rough surface of the wall.

To prevent the above phenomenon, in the rotational cutting, the moment that the edge portion is cut into the wall the edge portion must repeatedly be raised so as not to pierce the root apex and not to be locked, which forces excessive moral pressure upon a dentist. In a dental handpiece incorporating the rotation and the back and forth movements, the above-mentioned problems will be overlapped.

SUMMARY OF THE INVENTION

It is therefore an object of the present invention to provide a dental handpiece stably cutting a wall of a root canal without a fear of piercing an apical foramen of the dental root. To accomplish the above objective, a dental handpiece according to the present invention comprises: means for holding a tool cutting a tooth to be cured; and a support for setting the cutting tool at a desired position relative to the tooth to be cured.

In the above dental handpiece, the length of the support may be changeable by stages; the holding means may comprise a head of the dental handpiece, and a plurality of supports with different lengths may be removably mounted to the head; the support can stand on a head of the dental handpiece; length of the support projecting from the head is changeable; the support is to separately be formed from the dental handpiece so as to be removably mounted thereto; the support may have a stopper; and the support can abut with a tooth to be cured or an appropriate portion near the tooth.

In case of a rotation type dental handpiece, when a cutting tool driven by the handpiece cuts a root canal, a support is mounted to the handpiece, and the support abuts with a tooth to be cured or an appropriated portion near the tooth, which allows load applied to the cutting tool to be dispersed since the support receives a part of the load. In addition, the posture of the handpiece in cutting operation can be maintained to conduct stable cutting operation.

In case of a back and forth movements type dental handpiece, force applied to a cutting tool is transmitted to a support, and there is no fear of engagement or locking of the cutting tool, which allows continuously stable cutting operation. And, the up and down movements of the head accompanied by the engagement or locking of the cutting tool can be mitigated, and the movement of a hand is also prevented.

In both rotation type and back and forth movements type dental handpieces, the engagement and breakage of the cutting tool are prevented, therefore, wear of the cutting tool can be decreased so that the life thereof will become long; and the number of works for replacing the cutting tool is also decreased to shorten a period of time for cure.

BRIEF DESCRIPTION OF THE DRAWINGS

The present invention will be more apparent from the ensuring description with reference to the accompanying drawings wherein.

DETAILED DESCRIPTION OF PREFERRED EMBODIMENTS

The dental handpiece according to the present invention will be described in detail with reference to the accompanying drawings wherein like numerals refer to like parts throughout.

Figure 1:
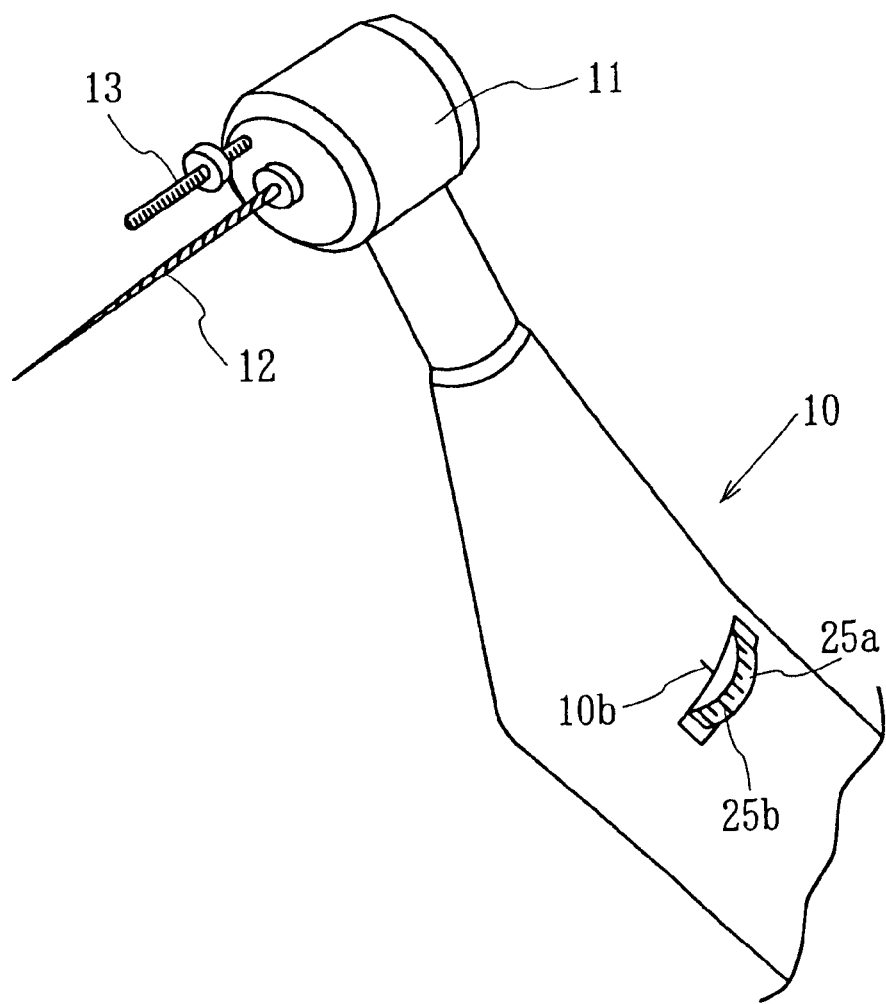
FIG. 1 is a perspective view of a primary portion of a dental handpiece according to one embodiment of the present invention.

The perspective view of FIG. 1 shows a primary portion of the dental handpiece of the present invention. In the dental handpiece 10 illustrated in the figure, a cutting tool 12 is attached to a head 11 as a holding means, and a support 13 is provided adjacent to the cutting tool 12. The support 13 is a point of the present invention. The support 13 is made from a material, such as metal, of which length scarcely change even though it is compressed. The tip of the support 13 is preferably covered with rubber or the like to prevent slippage and relieve contact force.

Figure 2:
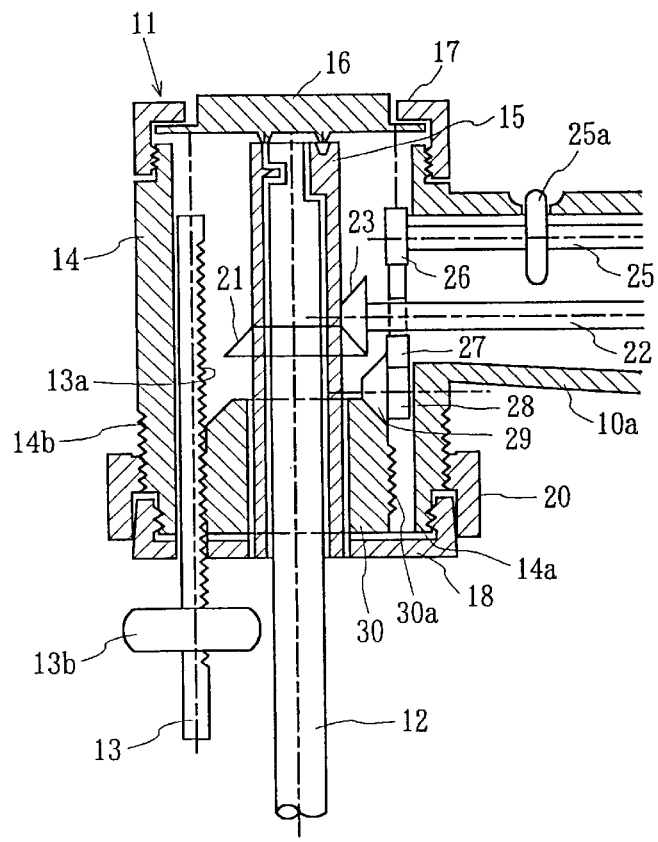
FIGS. 2A and 2B are a cross-sectional view and a bottom view respectively of the dental handpiece illustrated in FIG. 1.
Figure 2:
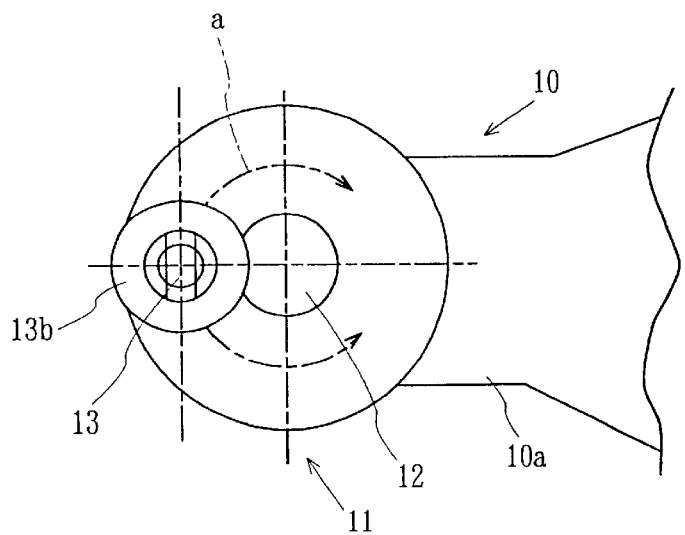

FIG. 2 is a cross-sectional view of the head 11. A frame 14 of the head 11 is a hollow and short cylinder so as to be mounted to a tip of a hollow main body frame 10a of the dental handpiece 10 while crossing the tip at right angles. The insides of the main body frame 10a and the frame 14 of the head 11 are continuous with each other.

The frame 14 of the head 11 rotatably holds therein a tool chuck 15 for holding the cutting tool 12. And, at the rear end (the upper end in FIG. 2A) of the frame 14, a rear cap 16 is mounted to prevent the retreat of the tool chuck 15, and a ring 17 that is screwed to the frame 14 of the head 11 fixes the rear cap 16.

The front end of the frame 14 of the head 11 is thin, and a front cap 18 is mounted to the thin portion 14a. Uneven portions are formed on the thin portion 14a and the front cap 18, and after the uneven portions are fit, the front cap 18 is not removed even if it is drawn in a direction of the central axis thereof, but the front cap 18 is rotatable about the central axis. The outer surface of the front cap 18 is tapered toward the upper part of FIG. 2A. On the other hand, at the large diameter portion of the outer surface of the frame 14, a male screw 14b is formed, and a fastening ring 20 is adapted to the male screw 14b. After the uneven portion inside of the front cap 18 is fixed to the uneven portion of the thin portion 14a at the tip of the frame 14, the fastening ring 20 is rotated so as to be lowered toward the lower part of FIG. 2A, which allows the front cap 18 to be tightened and fixed from outside at the inner face of the fastening ring 20.

The cutting tool 12 is inserted into the central hole of the front cap 18, and into another hole apart from the center is inserted the support 13. When the fastening ring 20 is loosened with the support 13 being inserted, as described above, the front cap 18 becomes rotatable about the cutting tool 12. On the other hand, the support 13 is movable within the range of a circular arc a indicated by a two-dot-chain line in FIG. 2B in the space that is formed inside of the frame 14 of the head 11 if it is not interfered with other parts. Therefore, a user sets the support 13 at a desired place and secures it with the fastening ring 20 to fix the support 13 at a desired position on the circular arc a.

Outside of the tool chuck 15, a bevel gear 21 is integrally formed with the tool chuck 15. The bevel gear 21 engages with a bevel gear 23 that is secured to the tip of a drive shaft 22 that is inserted into the main body frame 10a. The drive shaft 22 is driven and rotated by a motor or the like not shown. When a motor or the like rotates the drive shaft 22, the rotation is transmitted from the bevel gear 23 to the bevel gear 21, which allows the cutting tool 12 to rotate.

In the main body frame 10a is mounted another shaft 25 in parallel to the drive shaft 22. The shaft 25 is driven by another motor not shown. In the middle of the shaft 25, an operation ring 25a for manual operation is integrally formed with the shaft 25. A part of the operation ring 25a is exposed from an opening formed on the main body frame 10a, so that the operation ring 25a is operable by rotating with fingers or like from outside. On the outer surface of the operation ring 25a are cut graduations 25b, and the combination with the graduations 25b and a graduation 10b, which indicates a base position on the main body side and makes it possible to know the angle that the operation ring 25a rotates.

To the tip of the shaft 25 is secured a spur gear 26, and the spur gear 26 engages with a gear 27 which is rotatably mounted to the drive shaft 22, and the gear 27 engages the next gear 28. A bevel gear 29 is integrally formed with the gear 28.

To the tool chuck 15 is rotatably mounted a bevel gear 30 which engages with the bevel gear 29, and on the cylindrical portion at the lower part of the bevel gear 30 is formed a male screw 30a. On the other hand, the support 13 is accommodated in the frame 14 with a length so as not to be shaken at least. On the face opposite to the male screw 30a is formed a screw 13a like a lack, and the screw 13a engages with the male screw 30a. As a result, the support 13 becomes extendable.

The screw 13a is formed until a portion near the tip of the support 13 projecting from the front cap 18 to outside, and in the middle of the projecting support 13 is mounted a stopper 13b. The stopper 13b is formed like a disk, and is provided with an uneven portion at the central hole. When the stopper 13b is rotated under the condition that the uneven portion and screw 13a not shown formed on two faces which are on the outer surface of the support 13 and cross the surface on which the screw 13a is formed, the position of the stopper 13b goes up and down.

Next, with reference to FIGS. 3 to 10, the usage of the dental handpiece according to the present invention in crown down method will be explained. The crown down method is a method of forming a root canal from a root canal opening to a root apex by gradually changing files from thicker one to thinner one.

Figure 3:
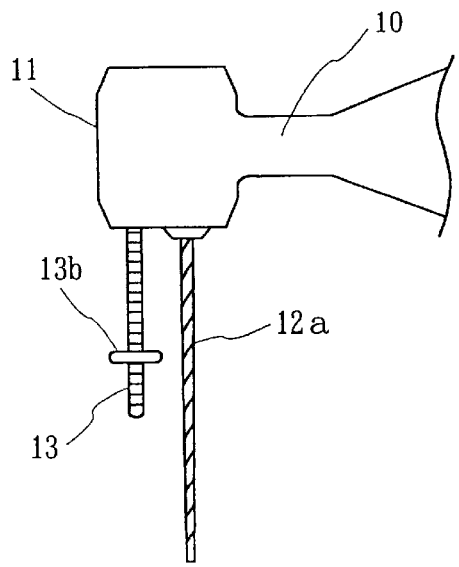
FIG. 3 is a side view of the dental handpiece according to the present invention to which a cutting tool and a support are mounted.

At first, as illustrated in FIG. 3, to the dental handpiece 10 according to the present invention is mounted a thin file 12*a* as the cutting tool 12, and the support 13 is extended to move the stopper 13*b* to a position near the tip of the support 13. The file 12*a* used here is to measure the depth to a root apex and not to cut a root canal. However, the length of the file 12*a* definitely corresponds with that of the cutting tool 12*b* actually used.

Figure 4:
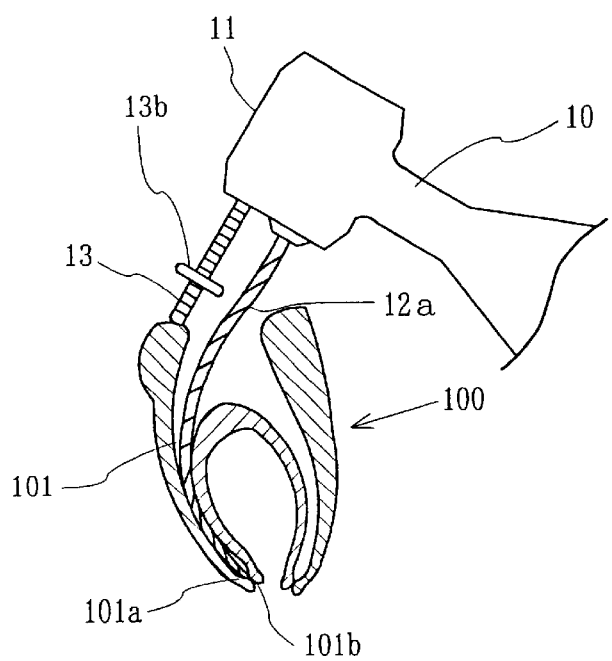
FIG. 4 is a drawing showing a condition that the depth of a root canal of a tooth to be cured is measured.

Next, as illustrated in FIG. 4, the thin file 12*a* is inserted into a root canal 101, to be cut, of a tooth 100 to be cured, and the tip of the support 13 is pressed to an appropriate position on the tooth 100. Then, the length of the support 13 is gradually shortened so that the file 12*a* proceeds in the root canal 101 and the tip of the file 12*a* reaches the root apex 101*a*.

In this operation, the length of the support 13 is changed by rotating the shaft 25 by a motor or the like and transmitting the rotation to the spur gear 26, gear 27, gear 28, bevel gear 29, bevel gear 30, male screw 30*a*, and screw 13*a*. It is also possible to change the length of the support 13 by manually rotating the operation ring 25*a* to rotate the shaft 25 and transmit the rotation in the same manner as described above. Then, when the tip of the file 12*a* reaches the root apex 101*a* as shown in FIG. 4, the shaft 25 is stopped to hold the length of the support 13 at the place. It is also possible to measure the distance to the root apex by X-rays, root canal length measuring device or the like in advance and decide the length of the support 13.

Figure 5:
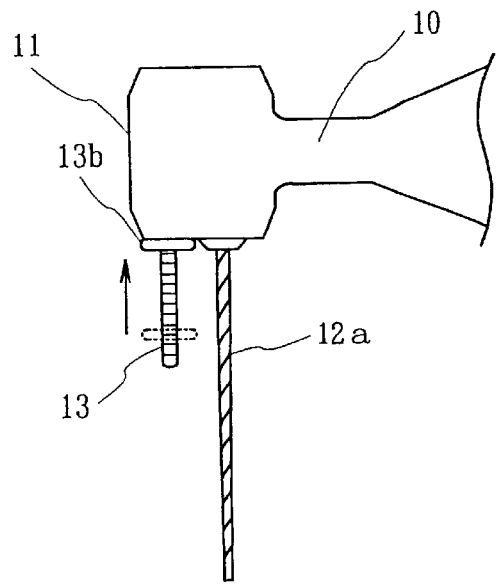
FIG. 5 is a drawing showing a condition that the position of a stopper of a support is adjusted.

Next, as shown in FIG. 5, the stopper 13*b* is moved on the base end side until it reaches the front cap 18, which determines the position where the length of the support 13 becomes shortest. After that, the support 13 is able to move in its projection direction but is not able to move in a direction that the support 13 is drawn back in the head 11.

Figure 6:
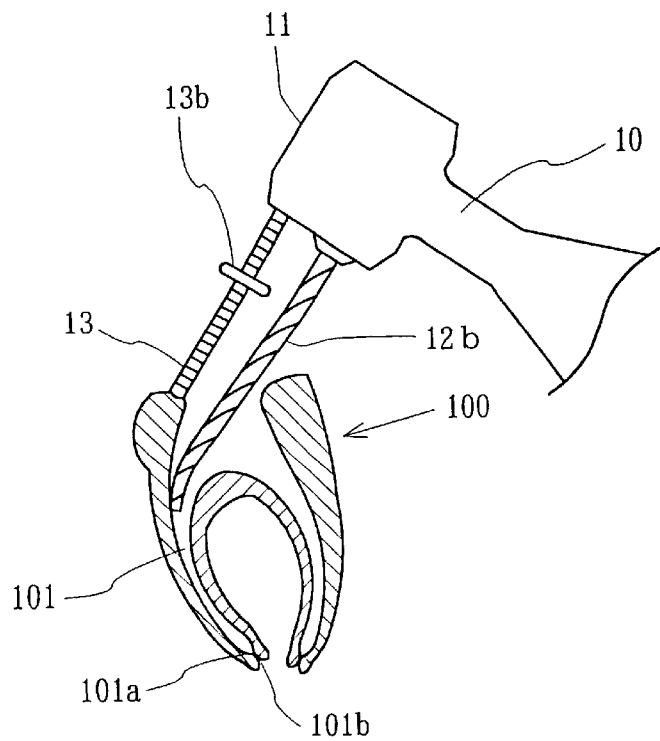
FIG. 6 is a drawing showing a condition that the cutting of a root canal of a tooth to be cured is initiated.

Next, as illustrated in FIG. 6, the cutting tool 12 is changed to the cutting tool 12*b* that is actually used to form a root canal. Then, the shaft 25 is rotated and the support 13 is extended to abut the tip of the support 13 against the tooth 100. Then, the tip of the cutting tool 12*b* is inserted into the root canal 101, and the cutting operation is initiated from an inlet of the root canal 101. Abutting the tip of the support 13 against the tooth 100 allows the posture of the dental handpiece 10 to be stable, resulting in easy cutting operation.

The current for driving a motor, which rotates the shaft 22, is large in cutting operation and small in mere racing without cutting operation. Therefore, when the magnitude of the current lowers from a prescribed threshold value during monitoring the current, the cutting operation is judged to be finished, and the motor of the shaft 25 is rotated to shorten the support 13. At this moment, the rotation of the shaft 25, and a period of time that the motor driving the shaft 25 is operated, and so on are determined in such a manner that the support 13 is shortened by a prescribed length. With this method, it is possible to shorten the support 13 one step by one step (for instance, 0.1 mm by 0.1 mm)

With the graduations 25*b* of the operation ring 25*a*, it is confirmed that the cutting tool 12*b* proceeds by a distance desired for cutting with the cutting tool 12*b* (for example, 1 mm), and the cutting tool 12*b* is replaced with one rank thinner one. At this moment, the distance subjected to be cutting operation so far is equal to the length that the support 13 is shortened, therefore, it is possible to continue cutting operation with the new cutting tool 12*b* from the position that the cutting operation with the previous cutting tool 12*b* is finished.

Figure 7:
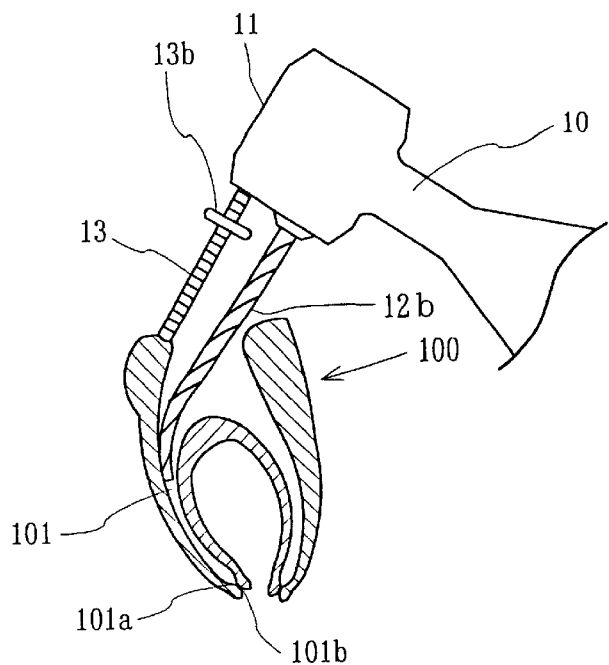
FIG. 7 is a drawing showing a condition that the root canal of the tooth is being cut.
Figure 8:
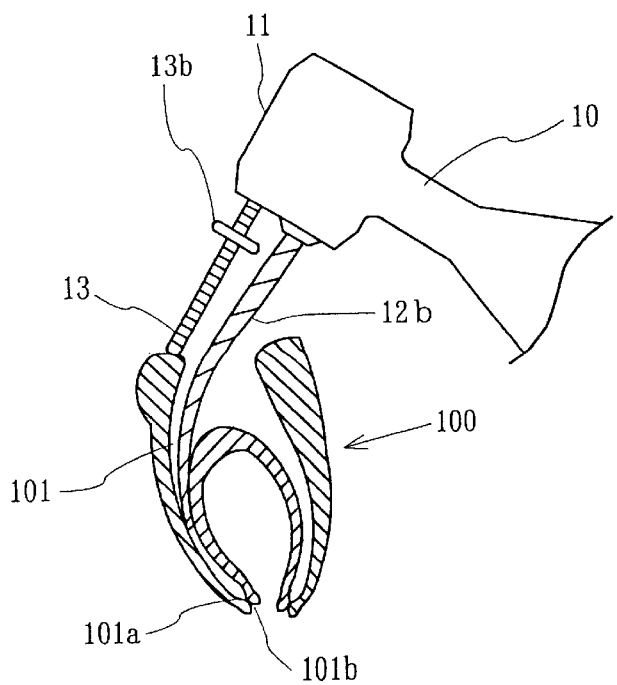
FIG. 8 is a drawing showing a condition that the root canal of the tooth is being cut.
Figure 9:
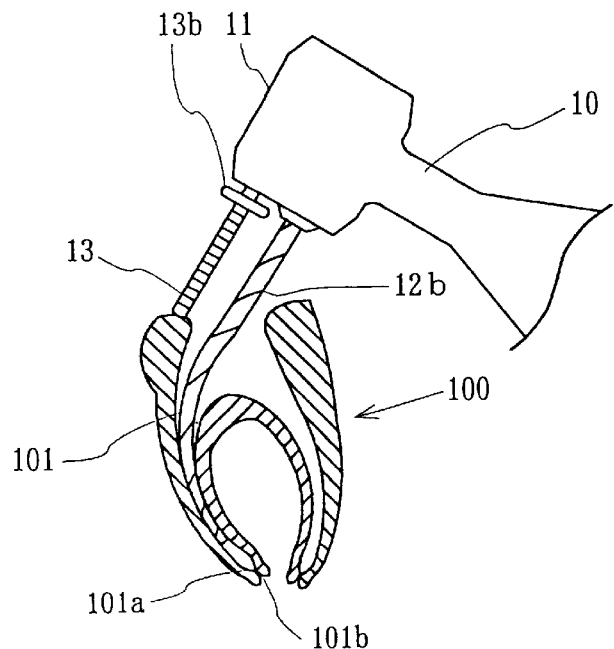
FIG. 9 is a drawing showing a condition that the root canal of the tooth is being cut.

FIG. 7 shows a step next to the step shown in FIG. 6. When the cutting operation in this stage is finished, the cutting tool becomes one rank thinner again as illustrated in FIG. 8 for another cutting operation. Then, the cutting tool changes from FIG. 8 to FIG. 9 and FIG. 10, and the stopper 13*b* contacts with the head 11 to prevent the stopper 13*b* from being shortened further. Therefore, with the cutting tool 12*b*, it is possible to cut until the root apex 101*a* neither more nor less. Then, during the above cutting operation, since the support 13 always abuts against the tooth, the posture of a dental handpiece is stable to form a smooth root canal.

Further, in rotational cutting, it is possible to control the force drawing the cutting tool 12*b* toward a root apex by the support 13, which prevents an edge of the cutting tool 12*b* from being broken due to its cutting into a wall of the root canal and prevents a wall face from becoming rough. Further, it is possible to determine the deepest position where the cutting tool 12*b* can reach by the stopper 13*b*, which prevents the cutting tool 12*b* from piercing the apical foramen of the dental root 101*b* too.

Still further, since the length of the support 13 is changed one step by one step during cutting operation, not only the cutting tool does not excessively enter the wall of a root canal but also smooth cutting operation is performed gradually deep into a root canal.

Figure 10:
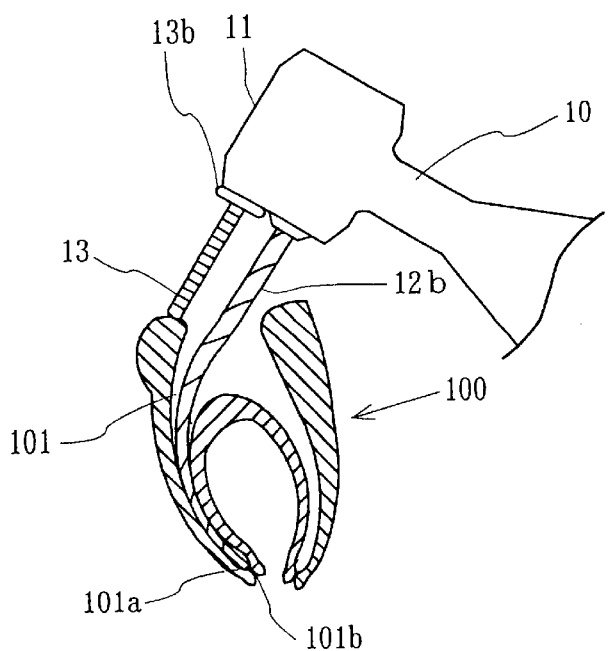
FIG. 10 is a drawing showing a condition that the cutting operation of the root canal of the tooth is completed.

In the above embodiment, a root canal is gradually cut from an inlet to a root apex, on the contrary, it is possible to insert a cutting tool into an root apex first and conduct the steps illustrated from FIG. 10 to FIG. 6, that is in a reverse order described above. In other words, the cutting tool can be adapted to the step back method that cuts the root canal while returning a cutting tool to the inlet one step by one step.

In the above embodiment, a dental handpiece for rotating the cutting tool 12 is adopted. The present invention can also be applied to a dental handpiece for moving a cutting tool back and forth. In case of the back and forth movements type, the force applied to a cutting tool is transmitted to a support, which allows stable cutting operation without fear of engagement or locking of a cutting tool. It is also possible to prevent the up and down movements of a head and of the movement of a hand due to the engagement or the like.

Further, in the above embodiment, a motor rotates the shaft 25, however, it is possible to change the length of the support 13 by manually rotating the operation ring 25*a* with fingers. In this case, the rotational angle of the operation ring 25*a* can be grasped from the graduations 25*b* of the operation ring 25*a* and the graduation 10*b*bindicating the base position on the main body side, which makes it possible to shorten the length of the support 13 one step by one step.

Still further, in the aforementioned embodiment, the length projecting from the head 11 is changeable by the screw 13*a* formed on the support 13. It is also possible to form a hole to insert and secure a support to the head 11 and use the support without screws by inserting into the hole. In this case, the length of the support is constant, that is, unchangeable, so that supports with a variety of lengths are prepared to use the supports by changing it in each step. With this construction, the structure of a dental handpiece becomes simple, resulting in low manufacturing cost. Further, a construction in which pluralities of supports are simultaneously used provides stabler cutting operation. It is possible to use soft material for the tip of a support to support with wider area since the tip is widened when pressing to a tooth or the like. Instead of a bar type support, a cylindrical support for enclosing a cutting tool may be used.

In the above embodiment, the stopper 13b contacts with the front cap 18 to prevent the cutting tool 12b from proceeding the position. It is also possible to detect by a micro switch not shown or the like that the stopper 13b contacts with the front cap 18 and stop the movement (rotation, back and forth movements, etc.) of the cutting tool 12b and automatically extend the screw 13a at the same time. With this construction, the cutting tool 12b is to be drawn out with ease.

Figure 11:
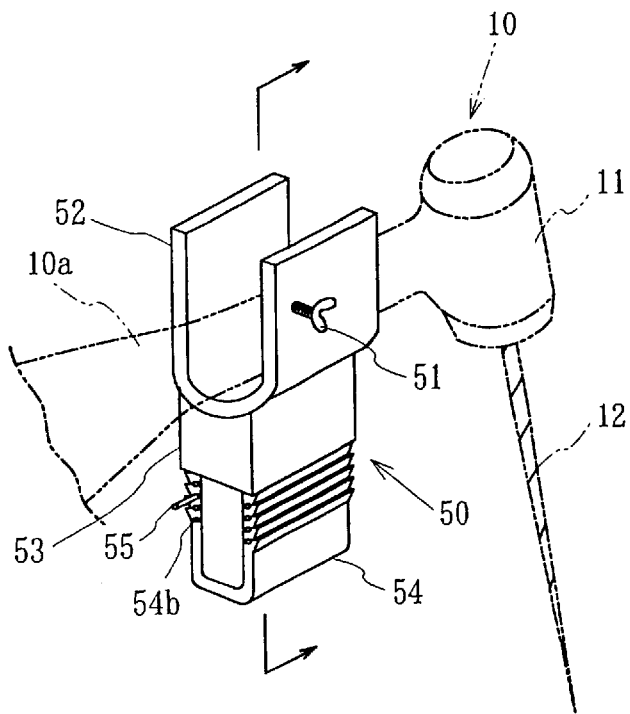
FIG. 11A is a perspective view of a support according to another embodiment of the present invention.
FIG. 11B is a cross-sectional view of the support shown in FIG. 11A.
Figure 11:
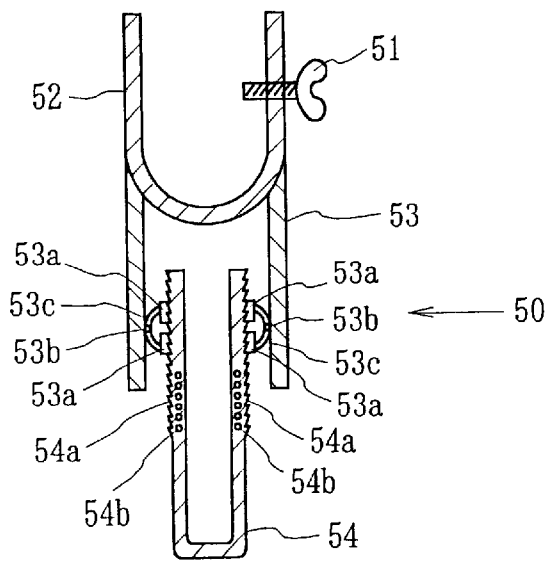

FIG. 11A shows a support according to another embodiment. In the previous embodiment, the support 13 abuts against the tooth 100 to be cured. The present invention is not limited to this type. A support according to this invention may abut against other tooth, other portion in a mouth or a part of a face and a body. In this embodiment, a support 50 is replaceablly mounted to the main body frame 10a of the dental handpiece 10, and the dental handpiece 10 is attached and fixed to the support 50 by fastening with a thumbscrew 51 in use.

FIG. 11B is an exploded cross-sectional view of the support 50. The support 50 comprises a U-shaped supporting portion 52 at a top of the support 50, a rectangular and cylindrical case 53 integrally formed with the supporting portion 52 from the lower portion thereof, and a U-shaped and resilient contact portion 54 separately made from the supporting portion 52 and the case 53. Outside of a face opposite to the contact portion 54 are formed sawtooth portions 54a, and inside of the case 53 are mounted bow-shaped portions 53c with two engaging portions 53a which engage with the sawtooth portions 54a, and the bow-shaped portions 53c are supported by supporting points 53b on the inner wall of the case 53. With this construction, the bow-shaped portions 53c are rotated about the supporting points 53b by a button not shown to reciprocate the two engaging portions 53a one after another, which allows the contact portion 54 to be shortened one step by one step. Pluralities of holes 54b are drilled on the side of the contact portion 54 to insert the pin 55 as a stopper thereto.

The main body frame 10a of the dental handpiece 10 is inserted into the U-shaped space of the supporting portion 52, and the thumbscrew 51 is fastened to fix the dental handpiece 10. A thin tool as the cutting tool 12 is attached to measure the depth to a root apex. The contact portion 54 is abutted with an appropriated portion in or out of a mouth. In order to stabilize the position of the contact portion 54, it is preferable to abut the contact portion 54 with a hard portion such as a tooth and a bone.

Hereinafter, it is possible to conduct a cutting operation in the order shown in FIG. 3 to FIG. 10 as described above. However, when the depth to a root apex is determined, the pin 55 is inserted to prevent the contact portion 54 from entering in the case 53 further. And, in order to shorten the support 50 one step by one step, a button not shown is depressed to change the position that the sawtooth-shaped engaging portions 53a and the sawtooth portions 54a engage with each other one pitch by one pitch.

In this embodiment, if only the support 50 is manufactured, a dental handpiece in the past is usable as it is. And, in place of the sawtooth-shaped engaging portions 53a and the sawtooth portions 54a, screws may be used. In place of the pin 55, push screws may be used. Like this, many options are possible. The support 50 is made from a transparent material such as plastic such that the cutting tool 12 can be observed.

As described above, the dental handpiece according to the present invention comprises: means for holding a tool cutting a tooth to be cured; and a support for setting the cutting tool at a desired position relative to the tooth to be cured. With this construction, the cutting tool stably forms a root canal, and it is easily prevented that the cutting tool pierces a apical foramen of the dental root.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A dental handpiece comprising:
   means for holding a cutting tool to cut a tooth to be cured;
   a support for setting said cutting tool at a desired position relative to the tooth to be cured;
   a stopper provided along said support so that cutting by the cutting tool would not exceed an intended depth of the tooth;
   a shaft; and
   a series of gears which transmit a rotational movement of said shaft to said support;
   wherein said support is used to alter the setting of the cutting tool to the desired position, and said stopper on the support is moveable along the support, and a movable length of said support is regulated by the position of said stopper which is changed in response to the rotational movement of said shaft transmitted through the gears.

2. The dental handpiece as defined in claim 1, wherein said shaft is driven by a motor.

3. The dental handpiece as defined in claim 1, further including an operation ring on said shaft to manually control the movable length of said support.

4. The dental handpiece as defined in claim 1, wherein a distal end of said support is fixed to a predetermined position when the cutting tool is in motion.

5. The dental handpiece as defined in claim 1, wherein said support is movable along an arc about an axis of said cutting tool.

* * * * *